United States Patent [19]

Daleiden

[11] Patent Number: 5,109,840
[45] Date of Patent: May 5, 1992

[54] RESUSCITATOR HAVING DIRECTIONAL CONTROL VALVE WITH INTERNAL "PEEP" ADJUSTMENT VALVE

[75] Inventor: John P. Daleiden, El Paso, Tex.

[73] Assignee: Specialty Packaging Licensing Company, Wilmington, Del.

[21] Appl. No.: 655,642

[22] Filed: Feb. 14, 1991

[51] Int. Cl.[5] .......................... A62B 7/04; A62B 9/02; A61M 16/00
[52] U.S. Cl. .......................... 128/205.13; 128/205.24; 128/204.28; 128/205.23
[58] Field of Search .................. 128/204.18, 204.28, 128/205.11, 205.13, 205.14, 205.24, 204.25, 205.23

[56] References Cited

U.S. PATENT DOCUMENTS

| | | | |
|---|---|---|---|
| Re. 32,553 | 12/1987 | Bennett et al. | 137/271 |
| 1,244,661 | 10/1917 | Teter | 128/205.24 |
| 1,896,716 | 2/1933 | McKesson | 128/205.24 |
| 3,575,206 | 4/1971 | Ulmann | 128/207.12 |
| 3,710,780 | 6/1973 | Milch | 128/207.14 |
| 4,182,366 | 1/1980 | Boehringer | 137/510 |
| 4,207,884 | 1/1980 | Isaacson | 128/200.24 |
| 4,345,593 | 8/1982 | Sullivan | 128/204.26 |
| 4,433,685 | 2/1984 | Giorgini et al. | 128/204.26 |
| 4,712,580 | 12/1987 | Gilman et al. | 137/859 |
| 4,774,941 | 10/1988 | Cook | 128/205.13 |
| 4,821,713 | 4/1989 | Bauman | 128/205.13 |
| 4,870,963 | 10/1989 | Carter | 128/205.24 |

FOREIGN PATENT DOCUMENTS

| | | | |
|---|---|---|---|
| 6701157 | 8/1967 | Netherlands | 128/207.12 |
| 1124703 | 8/1968 | United Kingdom | 128/207.12 |
| 1447091 | 8/1976 | United Kingdom | 128/205.24 |

Primary Examiner—Edgar S. Burr
Assistant Examiner—Kimberly L. Asher
Attorney, Agent, or Firm—Dallett Hoopes

[57] ABSTRACT

The directional control valve housing in a squeeze bag resuscitator includes a duck-bill element which permits inhaling from the bag as the duck-bill opens, and spontaneous exhaling as the periphery of duck-bill is pushed away from its seat. An adjustable spring urges the periphery against its seat with force established by the PEEP setting. The housing is in two screwed-together parts and the PEEP setting is effected by screwing the parts inward or outward.

5 Claims, 2 Drawing Sheets

Exhale-High PEEP

Exhale-Low PEEP

To Patient

Forced Inhalation

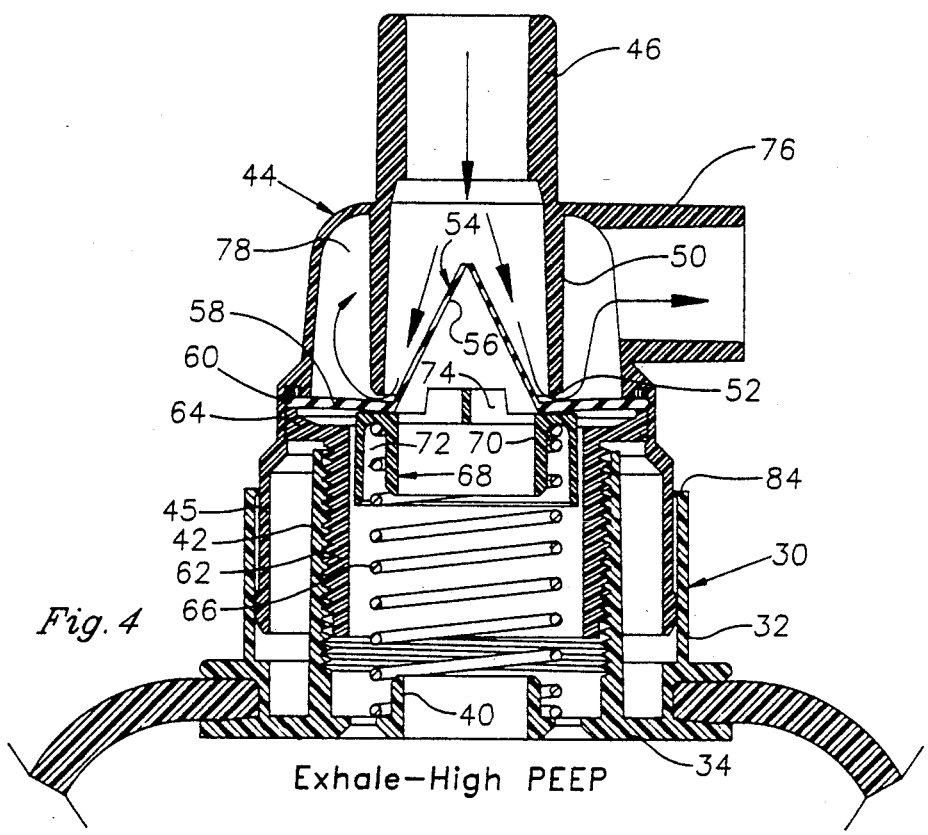
Fig. 4  Exhale—High PEEP
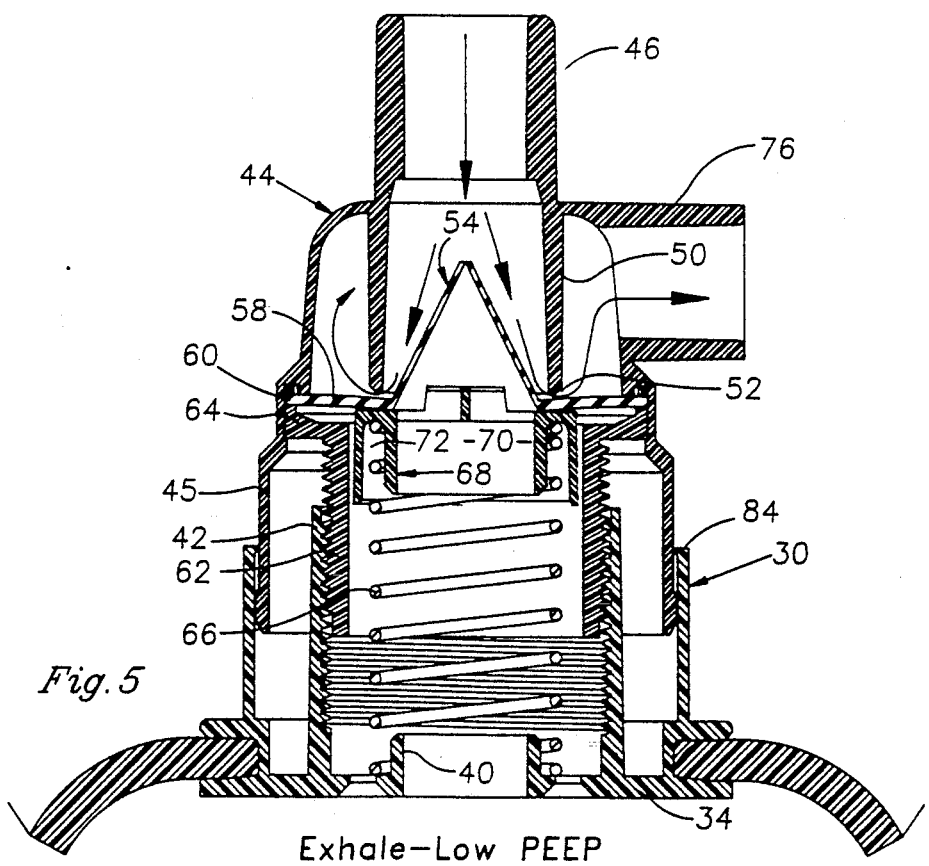
Fig. 5  Exhale—Low PEEP

RESUSCITATOR HAVING DIRECTIONAL CONTROL VALVE WITH INTERNAL "PEEP" ADJUSTMENT VALVE

BACKGROUND OF THE INVENTION

1. Field of the Invention

This invention relates to manual resuscitator systems. More specifically, this invention relates to resuscitation bags having directional control valves and means for controling the "PEEP" or Positive End Expiratory Pressure.

2. Description of Related Art including Information Disclosed under §§1.97 to 1.99

Manual cardiopulmonary resuscitation devices, utilizing self-inflating squeeze bags are well known in the prior art. An example, for instance, is shown in U.S. Pat. No. 4,774,941 which issued Oct. 4, 1988, to Wallace F. Cook. Also, there are earlier patents. Representative examples are:

U.S. Pat. No. 3,009,459 issued Nov. 21, 1961 to Henning Ruben

U.S. Pat. No. 3,262,446 issued Jul. 26, 1966 to George H. Stoner

U.S. Pat. No. 4,037,595 issued Jul. 26, 1977 to James O. Elam

U.S. Pat. No. 4,077,404 issued Mar. 7, 1978 to James O. Elam

U.S. Pat. No. 4,088,131 issued May 9, 1978 to James O. Elam et al

U.S. Pat. No. 4,121,580 issued Oct. 24, 1978 to Donald C. Fabish

U.S. Pat. No. 4,239,038 issued Dec. 16, 1980 to Ronald W. Holmes

U.S. Pat. No. 4,374,521 issued Feb. 22, 1983 to Thomas W. Nelson et al

During resuscitation with such devices, air or air enriched with oxygen is forced into the patient by squeezing the bag. The patient exhales through the valving system of the device. On release of the squeeze bag, the bag reinflates through a check valve. In addition to possessing the potential to force the desired flow and quantity of gases to the patient, such devices must take into account the fact that the patient may inhale or exhale spontaneously during treatment. These devices are therefore usually comprised of three basic elements: a mask, a specific directional control valve arrangement, and a squeezable bag.

These three elements have been well documented in the prior art. The mask must have sufficient flexibility to adjust to the contours of the face, while maintaining sufficient rigidity to allow for the application of enough force to create a seal during the direction of gas flow under pressure. The directional control valve must allow air to be forced under pressure to the patient, while still, as stated, allowing the patient to spontaneously inhale and exhale. An example of such a directional control valve is disclosed in U.S. Pat. No. 3,556,122 which issued Apr. 1971 to Asmund S. Laerdal.

Finally, the squeeze bag typically incorporates a check valve allowing air to fill the bag and must be of such construction as to be sufficiently compliant to allow 40 cycles per minute of operation while delivering a minimum of 500 cc. of air per cycle at 100 cm. of water pressure.

In addition to these three basic elements necessary to achieve the essential functions of cardiopulmonary resuscitation, there is frequently added a fourth element which is an external valve to provide measured and controllable resistance to the exhaled airflow, whether part of a forced cycle or spontaneous respiration. This element is known as a PEEP valve. The acronym PEEP as used in this case represents the term Positive End Expiratory Pressure, which is the aforementioned resistance to exhaled airflow at the preset pressure. The application of PEEP has long been recognized as a benefit to patients of cardiopulmonary resuscitation by maintaining a degree of inflation in the lungs, thus enabling a prolonged contact between the inhaled gases and the subject's pulmonary capillary bed, and preventing collapse of the lung.

In the past PEEP control valves have usually been separate from the air supply valve. The early U.S. Pat. No. 1,244,661 to Teter issued Oct. 30, 1917 discloses a mask provided with a valve for controlling the pressure during exhalation. The patent teaches that the device provides a "positive, adjustable pressure-valve" in order "to increase the absorption by the blood of the anesthetizing gas or vapors, and the lungs will not suffer collapse but may be distended thereby."

Another U.S. Pat. No. 1,896,716 to Elmer I. McKesson issued Feb. 7, 1933 discloses a mask having an exhaling valve with spring force adjustable by set screw to control exhalation pressure.

U.S. Pat. No. 3,710,780 issued Jan. 16, 1973 to Robert A. Milch has the patient exhale through a tube, the far end of which is dipped into water to an adjustable extent to control the exhalation pressure required.

The phrase "Positive End Expiratory Pressure" is used in the British patent 1,447,091 (1976) wherein a diaphram normally blocks the exhaust seat. A threaded nut with graduations adjusts the pressure on a spring to push the diaphragm against the seat to thereby adjust the amount of pressure required to exhaust the valve.

In the U.S. Pat. No. 4,182,366 issued Jan. 8, 1980 to John R. Boehringer a spring urges a diaphram to close an exhaust port. This patent uses the acronym "PEEP". A thumb screw can be adjusted to control the pressure on the spring.

The PEEP valve shown in U.S. Pat. No. 4,207,884 to Max Isaacson issued Jun. 17, 1980 comprises an annular seat and a disk-shaped valve. A spring urges the valve against its seat in accordance with the setting on a graduated plunger.

Two U.S. Pat. Nos. Re. 32,553 issued Dec. 30, 1980 to Clifford D. Bennett et al and 4,712,580 issued Dec. 15, 1987 to Keith Gilmanm et al are both directed to PEEP valves in which the opening of the exhaust valve is effected when the exhaling pressure raises the diaphram central of the valve to permit escape of air into the valve exhaust. The diaphragm is urged against the valve seat in each case by air pressure communicated through a tubular opening in the valve housing.

U.S. Pat. No. 4,345,593 issued Aug. 24, 1982 to John L. Sullivan and U.S. Pat. No. 4,433,685 issued Feb. 24, 1984 to Eugene A. Giorgini et al both include as a part of a mask an adjustible exit valve which would control PEEP (see FIG. 3 of both patents).

The U.S. Pat. No. 4,870,963 issued Oct. 3, 1989 to William Carter discloses a PEEP valve in which a valve element is pivotally mounted on a hub so that if one side of the valve is blocked, the valve can pivot open. Spring pressure is adjustable by turning a plunger.

While each of the four elements discussed above are recognized by the prior art, the prior art has perceived the resuscitation bag system with its valving as necessarily separate from the PEEP valve. The use of an external PEEP valve presents an inconvenience in emergency situations in which the resuscitation device is typically required. Its use also increases the cost of therapy and may be found to provide less effective therapy because there are two valves in the path of exhaled gases. First, the gases must pass through the aforementioned directional control valve integral to the resuscitation bag system known from the prior art. Then the exhaled gases must pass through the PEEP valve. This dual valving can potentially increase the resistance to exhaled gases in an unpredictable manner in the normal course of therapy and is therefore potentially detrimental.

SUMMARY OF THE INVENTION

The present invention addresses this problem by introduction of a PEEP valve which is integral with the resuscitation bag directional control valve system. It is therefore more convenient, less costly and potentially more therapeutically effective than devices described in prior art.

In the resuscitation device of the present invention, a squeeze bag is provided which includes a check valve to ensure one-way flow into the bag from outside room air or through an oxygen feed/reservoir system as known in the prior art. Also provided is a directional control valve assembly communicating with the bag and comprising a housing including a first cylindrical part secured to the bag and having a partial floor thereacross, the floor being formed with a perpendicular threaded sleeve concentric with the first cylindrical part. A second domed part is provided having an exit passage and an outlet port telescopingly related to the first part, the second domed part having associated therewith a second threaded sleeve disposed axially thereof, the first and second threaded sleeves being threadedly engaged.

A tubular patient port is joined to the domed part of the valve housing and adapted to be coupled in gas flow communication to the patient, said patient port extending into said valve housing and including a tubular extension formed concentric with the valve housing and having a circular end seat. A unitary flexible duck-billed diaphragm valve is provided including a flexible outer normally flat peripheral portion and an inner duck-bill portion. The peripheral portion is secured to the second domed part and is adjacent to and engageable with said circular end seat of said tubular extension, to close off the exit port. The duck-bill portion extends into the tubular extension. Spring means are disposed compressively between a annular portion of the duck-billed valve opposite the seat and the floor of the cylindrical first cylindrical part of the housing. The spring urges the valve to seat against the circular end seat.

By turning the first and second parts relatively, the PEEP setting may be accurately adjusted.

BRIEF DESCRIPTION OF THE DRAWINGS

Other features and objects of the invention will be apparent from the following specification and the drawings, all of which show a non-limiting embodiment of the invention. In the drawings:

FIG. 4 is a further enlarged centerline sectional view of the directional control valve housing during a patient's spontaneous exhalation, of the combined directional control valve and PEEP valve with the PEEP valve set at a relatively high PEEP; and FIG. 5 is a view similar to FIG. 4 but showing the PEEP valve at a relatively low setting.

DESCRIPTION OF THE PREFERRED EMBODIMENT

Figure 1:
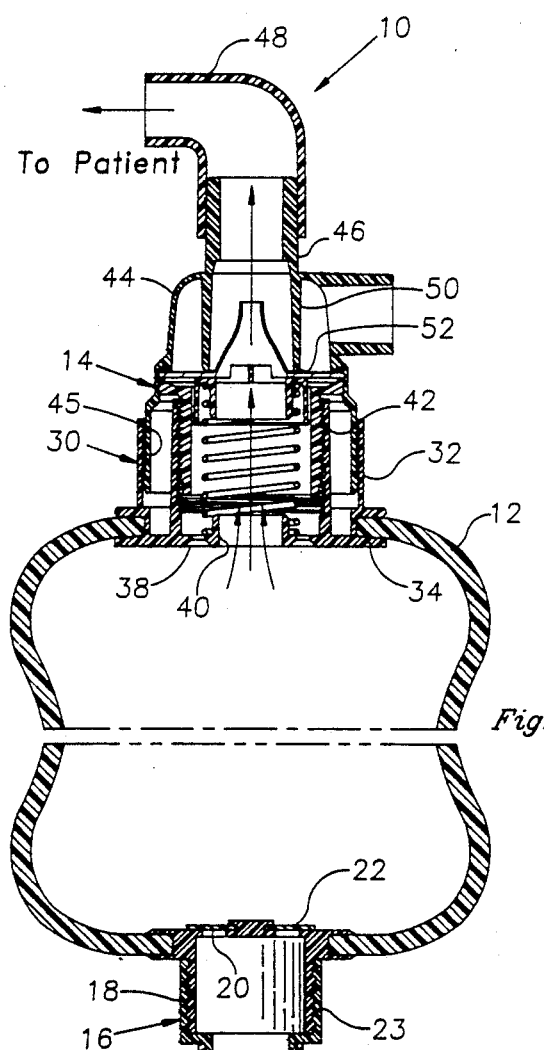
FIG. 1 is a broken, centerline sectional view of a resuscitator embodying the invention shown during a patient's forced inhalation.

A resuscitator embodying the invention is generally designated 10 in FIG. 1. It comprises a plastic squeeze bag 12 having two connections. A first connection generally designated 14 is linked to the patient by way of a mask (not shown) and controls the outlet of the bag and the exit port, and a second connection generally designated 16 connects the inlet of the bag to a gas source.

The inlet connection 16 is in the form of a two-part housing which includes a threaded fitting 18 having a pair of parallel annular flanges as shown between which the lower opening in the bag 12 is sandwiched as is conventional. Housing 18 is formed in its upper end with a plurality of openings 20 over which is attached an annular flapper valve 22. The flapper valve 22 defines a one-way check valve by which air and/or oxygen may be introduced into the bag 12 but not pass out.

Further, as is conventional, the fitting 18 has threaded over it a second part of the housing 23 which reduces to a sleeve 24 in which is supported a tubular spud 25 for receiving an oxygen connection. In use, an air supply hose 26 is connected to the sleeve 22 and an internal oxygen tube 28 disposed inside the air hose is connected to the tubular spud 25.

The first connection 14 is in the form of a two part housing which encloses a directional control valve assembly. The housing has a first cylindrical part 30 at the bottom of which are a pair of spaced annular flanges similar to those on connection 16. Between the flanges is sandwiched the upper opening of the bag 12.

Figure 3:
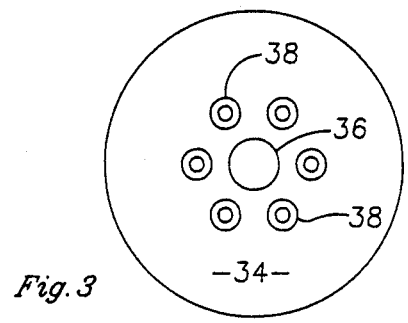
FIG. 3 is a bottom view of the lower part of the directional control valve housing on the scale of FIG. 1.

The first housing part 30 has extended from the upper flange a cylindrical wall 32. The bottom wall, or floor, 34 of the first housing part is formed with a central opening 36 (FIG. 3) about which are located a plurality of satellite holes 38 which may be countersunk as shown if desired or necessary. Around the opening 36 the floor is formed with an upward central hub 40. Further, inward from the cylindrical wall 32 and outward of the satellite holes 38 the floor is formed with a perpendicular internally threaded upward sleeve 42 concentric with the wall 32.

The housing 14 also comprises a second domed part 44. This part includes a downward cylindrical wall 46 which telescopes inside the wall 32 of the cylindrical first part 30. Molded integrally with the domed second part 44 is an axial tubular port 46 which is adapted to be connected to the patient through an elbow 48 and a mask, not shown. The tubular patient port 46 extends into the housing and includes a tubular extension 50 formed concentric with the housing and having a circular seat 52.

A unitary rubber flexible duck-billed diaphragm valve 54 is provided. It includes a bill portion 56 and a peripheral annular flat flange 58 (FIG. 4). As shown, the duck-billed portion 56 extends up into the extension 50. The flange 54 normally engages the seat 52 and the extreme periphery of the flange 58 is sandwiched between a shoulder o the domed second part 44 of the housing and a clamping surface 60 on the upper end of a second threaded sleeve 62. Sleeve 62 is exteriorly threaded and formed with an outward annular flange 64 on the upper outer portion of which the clamping surface 60 finds itself.

Figure 2:
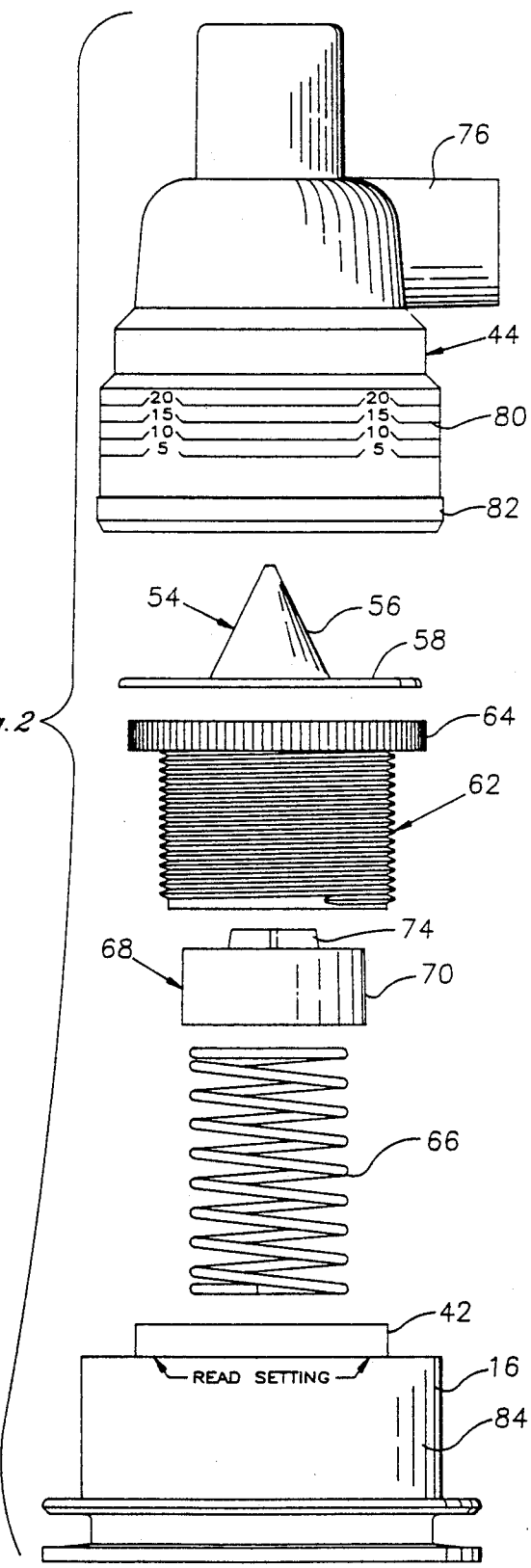
FIG. 2 is an enlarged exploded view of the combined directional control valve and PEEP valve.

The outer surface of the flange 64 (FIG. 2) is formed with a series of longitudinal ribs and grooves as is the interior of the second housing part 44 in this vicinity (not shown). The interfitting of the ribs and grooves on these two parts plus a staking in or sealing of the flange 64 in its place assure the unitary structure of the upper second housing part 44.

As shown (FIG. 4), the threaded lower portion of the sleeve 62 threads into the threaded portion of the upstanding sleeve on the second part 30 so that as the two parts are turned relatively the distance between the bottom of the extension 50 and the floor 34 changes.

Spring means are provided as shown. They comprise a spiral spring 66 and a spool-like element 68 which has a central opening 70 and an annular upward well 72 which receives the upper end of the spiral spring. An open cross-shaped centering element 74 has a central upward hump which prevents possible downward inversion of the duck-bill under extreme high PEEP. The upper end of the spool-like element engages the underside of the flange of the duck-bill valve and, because the spring is under compression, urges it upward toward its seat on seat 52. The lower end of the spiral spring hugs the tubular upstanding hub 40.

From the side of the domed second part a lateral tubular exit port 76 is provided which vents the annular space 78 inside the housing and around the tubular extension 50.

On the outside of the second domed part 44 (FIG. 2) indicia 80 appear. Further, an outward lip 82 is provided at the lower end of this resilient part. The lower end of the lip 82 is beveled as shown for lead-in purposes.

It will be seen that the upper annular rim 84 of the sleeve 30 is slightly thickened inward to engage the side wall of the second part 44 in the area of indicia 80. It is the indicia 80 on the domed second part which is at the level of the rim 84 of the cylindrical wall 30 which indicates the PEEP setting.

FIG. 4 shows a relatively high PEEP setting with the domed second part 44 screwed well into the cylindrical wall 30. Hence, a reading of "20" as a PEEP reading might he obtained by this relationship. On the other hand, with the domed second part 44 unscrewed to some extent, as shown in FIG. 5, the rim 84 is more apt to be at a setting of "10"—a lower PEEP setting.

It can be imagined that the pressure exerted on the flange of the duck-bill by the spool 70 and generated by the spring 66 will be greater for the FIG. 4 setting than FIG. 5 setting because the floor 34 is closer to the duckbill in FIG. 4 than in FIG. 5. Hence, a patient would find it would take more effort to exhale through the valve with the FIG. 4 setting than it would with the FIG. 5 setting.

The parts of the embodiment have now been disclosed and focus is invited to the operation of the invention.

The desired PEEP valve setting is first chosen and set by turning the first and second parts of the housing 15 relatively until the setting appears on part 44 above the rim 84. The air hose 26 and oxygen tube 28 are connected to the housing 16. The customary mask is attached to fitting 48 and installed onto the patient.

The attendant may force inhalation by squeezing the bag. Because gas in the bag cannot escape through the check valve 20, 22, gas opens the duck-bill 56 and flows into the mask. When this cycle is complete, the exhaled gas pushes down the periphery of the duck-bill 54 away from the seat 52 with whatever force the PEEP setting requires to overcome the force of spring 66. From this unseating, the exhaled gas goes out exit port 76.

Should the patient spontaneously breath in, he will suck gas from the bag 12 through the duck-bill 54 and exhale as described above.

The structure hereby disclosed is beneficial as described above in that without the provision of a second valve, a PEEP function is provided internally in a more or less conventional squeeze bag type resuscitator without extra external parts. The setting on the PEEP valve may be readily adjusted by screwing the second domed part 44 into or out of the second perpenducular cylindrical first part 30. The PEEP valve function is achieved in this relatively simple structure by reliable means.

While the invention has been disclosed in only one embodiment, it is susceptible to many changes and variations. The invention should be thought of, therefore, as having the scope of the following claim language or extensions of the patent exclusion based on reasonable equivalents.

What is claimed is:

1. A resuscitator having an internal PEEP adjustment and comprising:
    (a) flexible squeeze bag means having a hollow interior and first and second connections thereinto,
    (b) a one-way gas inlet valve fastened to said second connection, said inlet valve permitting gas flow into said hollow interior through said second connection,
    (c) a directional control valve assembly communicating with the said first connection and comprising
        1) a valve housing comprising a first cylindrical part secured to said first connection and having a partial floor thereacross, the floor being formed with a perpendicular threaded sleeve concentric with the first cylindrical part, and a second domed part telescopingly related to the first part, the second domed part having associated therewith a second threaded sleeve disposed axially thereof, the first and second threaded sleeves being threadedly engaged,
        2) a tubular patient port joined to said domed second part of said valve housing and adapted to be coupled in gas flow communication to a patient, said patient port extending into said valve housing and including a tubular extension formed concentric with said valve housing and having a circular end seat and a unitary flexible duckbilled diaphragm valve, an exit passage being formed between said second domed part and said extension and having an outlet port; said duckbilled diaphragm valve including a flexible outer normally flat peripheral portion, and an inner duck-bill portion, said peripheral portion being secured to said second domed part and being adjacent to and engageable with said circular end seat of said tubular extension, said duck-bill portion extending into said tubular extension; and 3) a spring means disposed compressively between the floor of the first cylindrical part of the housing and an annular portion of the duck-billed diaphragm valve opposite the seat, and urging the duck-billed diaphragm valve to seat against the circular end seat, 4) said first and second threaded sleeves comprising PEEP setting means for adjusting the PEEP exhaled against, said sleeves permitting relative rotation of the first and second parts of the housing of said control valve assembly, whereby relatively rotating the parts of the valve housing to move the floor toward or away from the seat puts more or less compression on the spring to adjust the PEEP exhaled against.

2. A resuscitator as claimed in claim 1 wherein the first and second parts are formed with relative external graduations to indicate PEEP settings as the two parts are turned relatively.

3. A resuscitator as claimed in claim 1 wherein the first and second connections are at opposite ends of the bag means.

4. A resuscitator as claimed in claim 1 wherein the second sleeve and the domed second part are two separate elements secured together and held from relative rotation by having interfitting longitudinal ridges thereon.

5. A resuscitator as claimed in claim 1 wherein the spring means includes a spiral spring and a spool-like element having a central opening and an annular well which receives an end of the spiral spring adjacent the annular portion.

* * * * *